(12) United States Patent
Ries et al.

(10) Patent No.: US 12,349,878 B2
(45) Date of Patent: Jul. 8, 2025

(54) SURGICAL NEEDLE SET AND METHOD FOR DETERMINING THE POSITION OF A SURGICAL INSTRUMENT

(71) Applicant: JOIMAX GMBH, Karlsruhe (DE)

(72) Inventors: Wolfgang Ries, Linkenheim (DE); Rainer Steegmüller, Gerlingen (DE)

(73) Assignee: JOIMAX GMBH, Karlsruhe (DE)

( * ) Notice: Subject to any disclaimer, the term of this patent is extended or adjusted under 35 U.S.C. 154(b) by 758 days.

(21) Appl. No.: 17/615,303

(22) PCT Filed: May 27, 2020

(86) PCT No.: PCT/EP2020/064716
§ 371 (c)(1),
(2) Date: Nov. 30, 2021

(87) PCT Pub. No.: WO2020/245002
PCT Pub. Date: Dec. 10, 2020

(65) Prior Publication Data
US 2022/0218316 A1  Jul. 14, 2022

(30) Foreign Application Priority Data
Jun. 5, 2019 (DE) .......................... 102019003965.3

(51) Int. Cl.
*A61B 10/02* (2006.01)
*A61B 17/00* (2006.01)
(Continued)

(52) U.S. Cl.
CPC ........ *A61B 10/025* (2013.01); *A61B 17/3472* (2013.01); *A61B 90/06* (2016.02);
(Continued)

(58) Field of Classification Search
CPC .......... A61B 10/025; A61B 2010/0258; A61B 90/06; A61B 17/16; A61B 17/320016;
(Continued)

(56) References Cited

U.S. PATENT DOCUMENTS 5,758,655 A * 6/1998 Como Rodriguez ........................ A61B 10/025 600/562
2004/0010236 A1 * 1/2004 Morawski ............ A61B 10/025 604/272

(Continued)

FOREIGN PATENT DOCUMENTS

| CA | 3071475 A1 | 3/2019 |
| DE | 19639615 A1 | 4/1998 |
| DE | 202017004822 U1 | 11/2017 |

*Primary Examiner* — Devin B Henson
(74) *Attorney, Agent, or Firm* — McGlew and Tuttle, P.C.

(57) ABSTRACT

In particular for automatically determining the position of a Jamshidi needle, the invention provides a surgical needle set comprising a hollow needle and an obturator, wherein the obturator has, starting a finite distance from its distal tip, a hollow space extending longitudinally in a proximal direction, wherein at least one proximal lateral outlet of the hollow space is provided within a handle part of the obturator, and wherein the hollow space is in connection with a passage of an adapter part of an adapter, which passage extends at a finite angle to the longitudinal extent of the hollow space.

14 Claims, 5 Drawing Sheets

(51) Int. Cl.
*A61B 17/34* (2006.01)
*A61B 90/00* (2016.01)

(52) U.S. Cl.
CPC ................ *A61B 2010/0258* (2013.01); *A61B 2017/00477* (2013.01)

(58) Field of Classification Search
CPC . A61B 17/3472; A61B 17/3403; A61B 34/20; A61B 2034/2051; A61B 2034/2055
See application file for complete search history.

(56) References Cited

U.S. PATENT DOCUMENTS

| | | |
|---|---|---|
| 2010/0081920 A1 | 4/2010 | Whitmore, III et al. |
| 2010/0174176 A1 | 7/2010 | Nagel et al. |
| 2013/0296691 A1* | 11/2013 | Ashe .................... A61B 5/6848 |
| | | 600/424 |
| 2017/0202611 A1* | 7/2017 | Shin .................... A61B 18/1206 |
| 2018/0085144 A1 | 3/2018 | McGillicuddy |

* cited by examiner

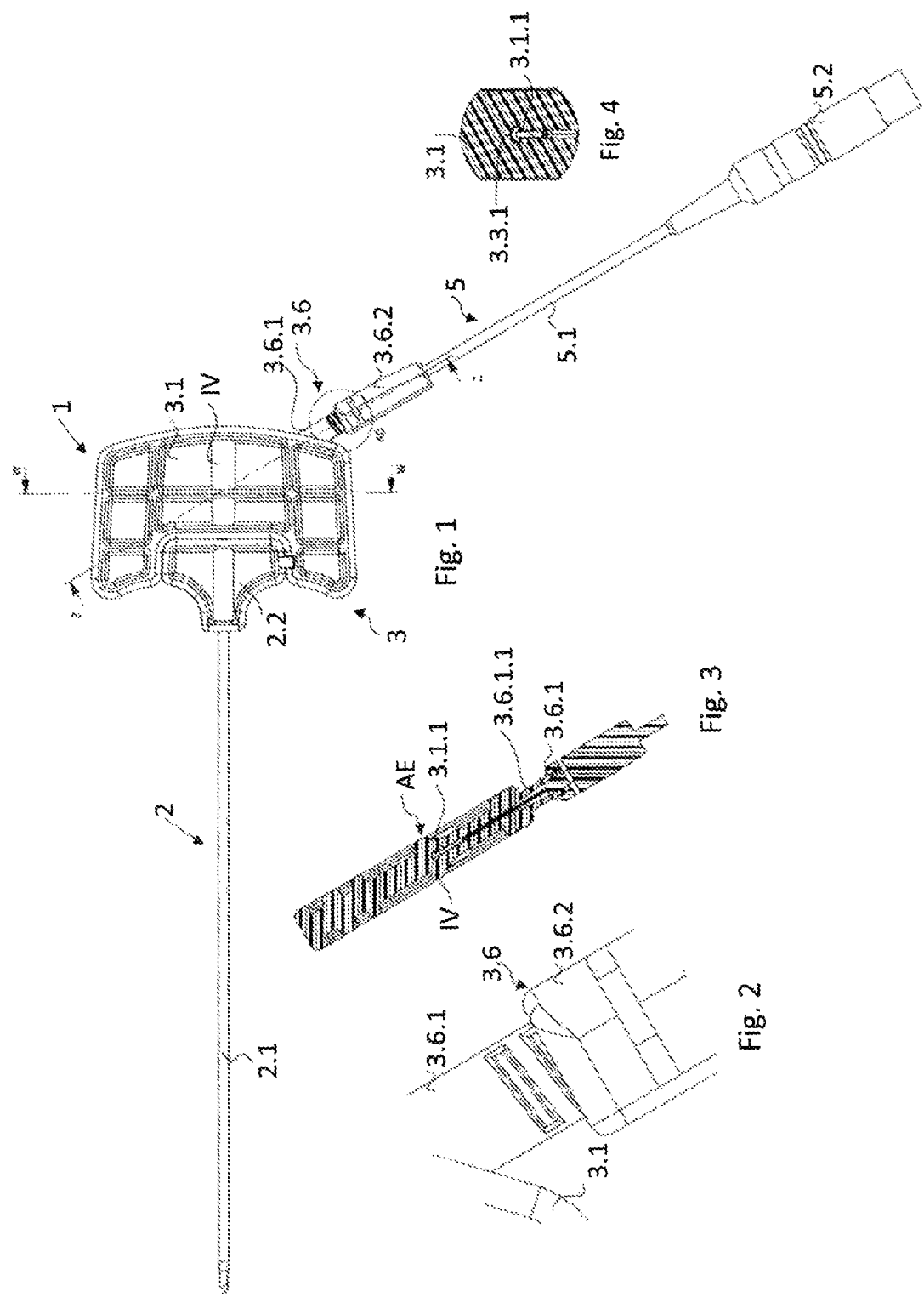

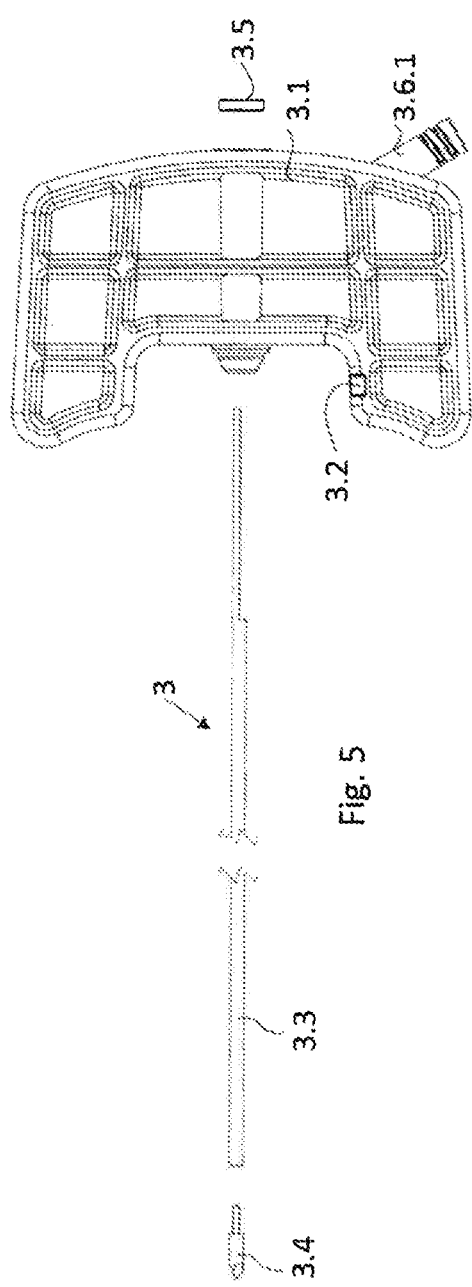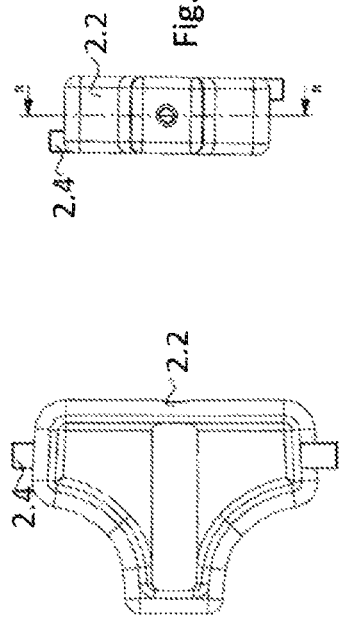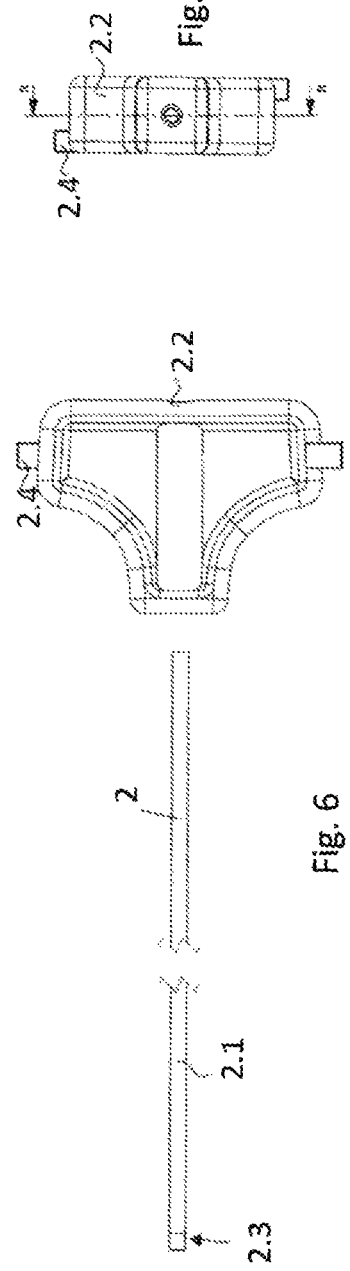

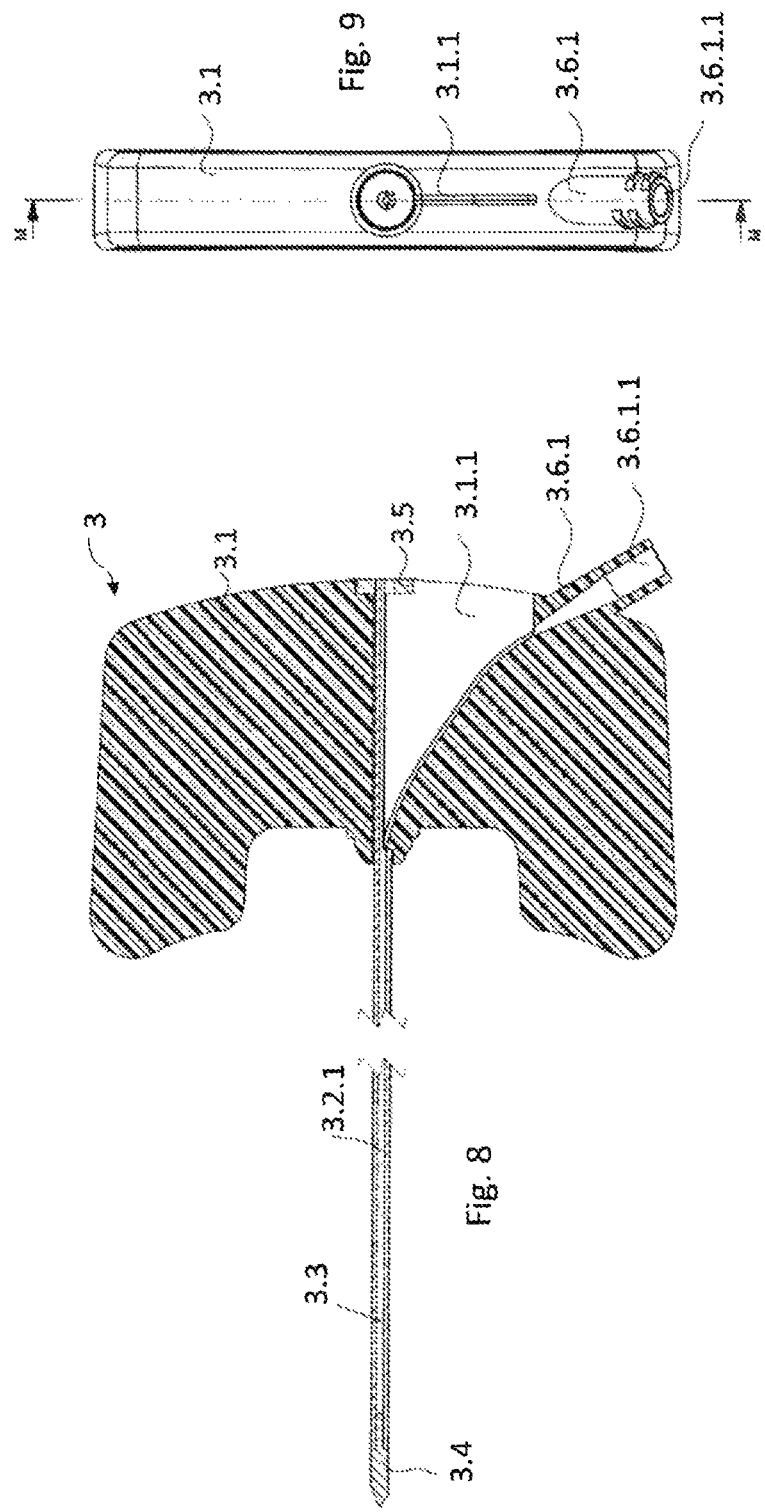

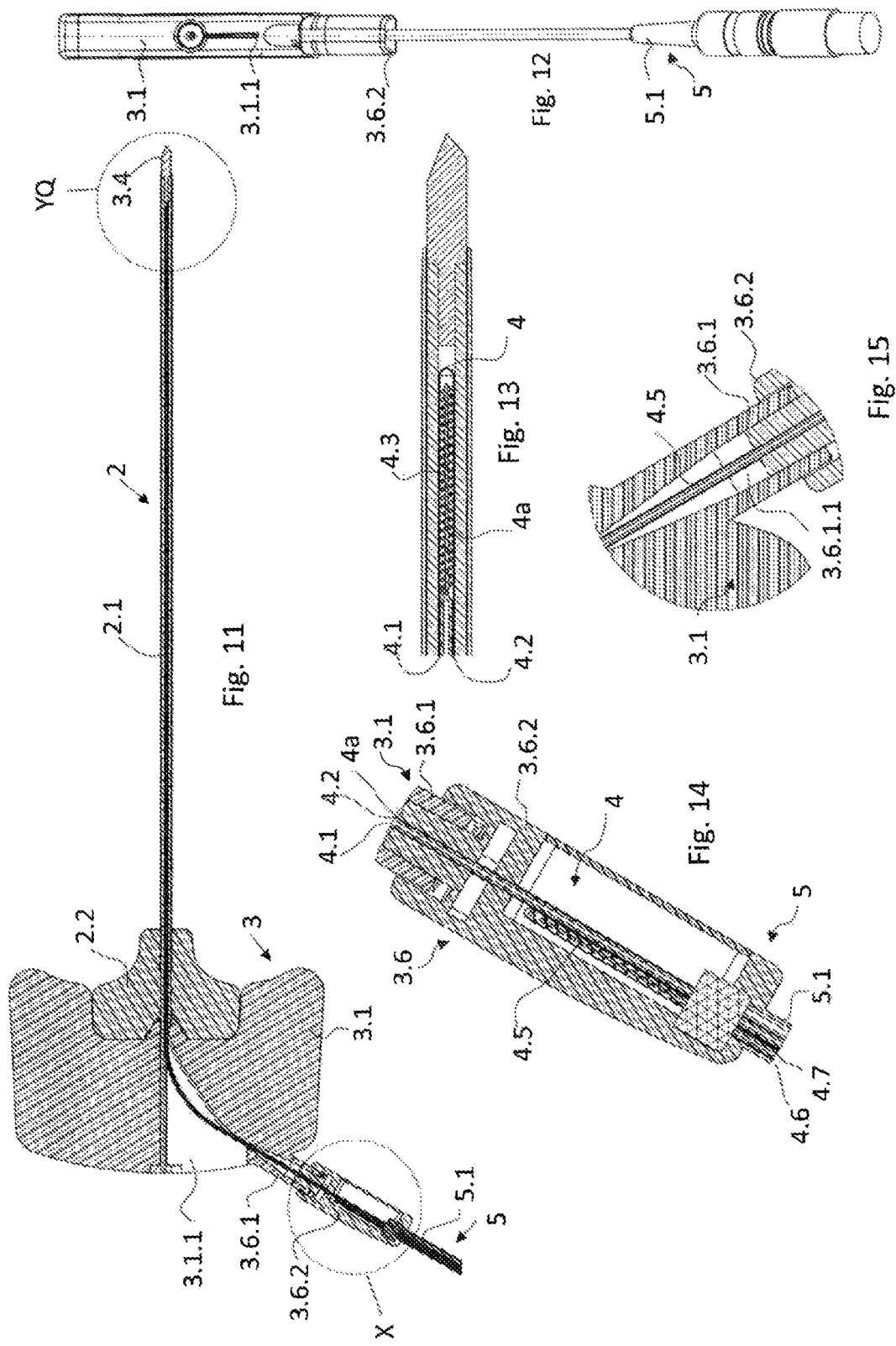

SURGICAL NEEDLE SET AND METHOD FOR DETERMINING THE POSITION OF A SURGICAL INSTRUMENT

The invention relates to a surgical needle set comprising a hollow needle and an obturator, and to a method for determining a surgical instrument.

Today, minimally invasive operations are already carried out using navigation-assisted surgical procedures. Various navigation systems are used for this purpose. Active and passive systems are used. In active systems, a part introduced into the body of a patient, such as an instrument or surgical tool, is provided with a transmitter, via which the trajectory and the position of the instrument or tool, in particular the distal end located at the point of intervention, can be determined externally.

In passive systems, in addition to optical systems for positioning a surgical instrument, in particular by its distal end, electromagnetic systems are also known. In electromagnetic navigation, an inhomogeneous electromagnetic field is generated by a field generator, which field is detected by one or more sensors, as a result of which the position and orientation of the instrument or surgical tool, in particular the distal end thereof, can be directly or indirectly detected in turn. Direct detection of the distal end of a surgical part involves arranging the sensor at the distal end of the part itself; indirect detection involves the fixed, rigid attachment of the sensor at a defined point, in particular an axial position, on the surgical part. Based on the measured sensor signal, conclusions can be drawn about the position and optionally the orientation of the distal end. In passive navigation, electromagnetic navigation, in which an electromagnetic field is generated externally around the operating area, for example by a generator of an electromagnetic field in a pillow on which the patient lies, has proven particularly successful. Coil-like sensors built into the surgical instrument allow the instruments to be located, whereupon CT or MRI images can be displayed. This X-ray method does not contain any radiation exposure and thus reduces radiation exposure overall, also through a reduced use of X-rays. The image quality is not impaired, and sensors cannot be obstructed since they are not optical sensors. The operator's freedom of movement is not restricted, as is the case in optical systems.

The invention relates in particular to the design of a hollow needle set generally referred to as a Jamshidi needle, which was first proposed by Khosrow Jamshidi in 1974 (https://en.wikipedia.org/wiki/Jamshidi_needle; https://www.cancer.gov/publications/dictionaries/cancer-terms/jamshidi-needle). This is an instrument consisting of a hollow needle in the form of a trephine and an obturator which is inserted through said needle and protrudes beyond the hollow needle distally, generally so as to be formed in the manner of a trocar. Both parts, the hollow needle and the obturator, have proximal handle parts by means of which they can be secured to one another. While the hollow needle and the solid obturator shaft are made of metal, the handle parts are made of plastics material. Such a Jamshidi needle is generally used for biopsy, in particular for bone biopsy, in order to remove bone marrow from a bone, such as in particular from a vertebral bone of the spinal column. Such a needle set is also used in orthopedic surgery for puncturing bones, especially vertebrae, as an access needle such as for kyphoplasty, for screw fastening, etc.

Systems are known in which an optical element, whether it is an optical transmitter or an optical sensor, is secured externally to the proximal end of such a Jamshidi needle (DE 196 39 615 A1).

In both cases, the attachment of an external part (whether it is an electromagnetic or optical sensor or an optical transmitter) on the actual instrument, here in particular a Jamshidi needle, is extremely disadvantageous, since such an element that protrudes proximally and thus radially in the handle region is extremely bothersome for the surgeon during the operation and can irritate them; in addition, due to the securing by clamping, said part can fall off or can shift relative to the instrument, in the former case the reassembly having to be done during the operation, in the latter case the relation to the distal tip, the position of which is determined on the basis of the detection system at a specified location of the sensor element or transmitter element, no longer being correctly identified. In addition, although such a transmitter element or sensor element secured proximally externally on an instrument, if said element is arranged fixedly on the instrument, can contribute the position to the determination of the position of the distal end of the instrument in space, it cannot contribute to the determination of the type of instrument itself, in particular before the start of the actual intervention on the patient by introducing the instrument into the patient.

The object of the invention is therefore that of providing a surgical needle set that allows automatic detection of the type of imaging surgical instrument by an evaluation or navigation system and provides a display adapted to the corresponding surgical instrument, in this case a Jamshidi needle, on a monitor of the navigation or evaluation system for the obturator.

According to the invention, the mentioned object is achieved by a surgical needle set which is characterized in that the obturator has, starting a finite distance from its distal tip, a hollow space extending longitudinally in a proximal direction, in that at least one proximal lateral outlet of the hollow space is provided within a handle part of the obturator, and in that the hollow space is in connection with a passage of an adapter part of an adapter, which passage extends at a finite angle to the longitudinal extent of the hollow space.

In a preferred embodiment, a sensor unit comprising a distal sensor and a proximal sensor extends through the passage of the adapter part to the distal end of the hollow space, the orientation of said latter proximal sensor enclosing a finite angle to the orientation of the former sensor due to the adapter part, in particular the relative angle between the first and the second sensor being between 10° and 90°, preferably between 50° and 70°, most preferably between 55° and 65°.

Further preferred embodiments of the invention are characterized in that the distal end of the obturator is in the form of a trocar, in particular an obturator tube being secured to a handle part of the obturator by means of a fixing ring fixedly connected to said tube, and/or in that the adapter part of the obturator is in the form of a Luer adapter part, and, moreover, in that the sensor unit has an adapter part, preferably a complementary Luer adapter part, that can be connected to the adapter part of the obturator.

In other embodiments according to the invention of the subject matter of the invention, the hollow needle and the obturator can be detachably connected to one another by means of rigid tabs of the handle part of the hollow needle, which tabs engage in lateral recesses of the handle part of the obturator, and/or in that the hollow needle is in the form of a trephine.

In addition, in a preferred embodiment of the invention, the sensor unit is inseparably connected to a connection cable, the connection cable in particular having a connection end for connection to an evaluation unit, and/or the sensors of the sensor unit are in the form of coils, to the distal and proximal ends of each of which an electrical line is connected. Instead of a wire signal line, wireless transmission from a sensor unit to a control unit is also possible.

An instrument set consisting of the hollow needle and the obturator is characterized by one or more features of the obturator of the needle set.

To achieve the object according to the invention, the hollow needle and the obturator are connected relative to one another so as to have fixed positions, but so as to be detachable, and the obturator is designed such that the obturator has, starting a finite distance from its distal tip, a hollow space extending longitudinally in the proximal direction, that at least one proximal lateral outlet of the hollow space is provided within a handle part of the obturator, that the hollow space is in connection with a passage of an adapter part of an adapter, which passage extends at a finite angle to the longitudinal extent of the hollow space, and that the angular orientation of two sensors of a sensor unit, which sensors are arranged at a fixed longitudinal distance from one another, is determined.

Further advantages and features of the invention can be found in the claims and in the following description, in which an embodiment of the invention is explained in detail with reference to the drawings, in which:

FIG. 1 is a schematic overall representation of a surgical needle set according to the invention;

FIG. 2 is an enlarged representation of the detail AD of FIG. 1 with two interconnected adapter parts of an adapter in the form of a Luer adapter;

FIG. 3 shows a section along the line Z-Z in an extension of the adapter of FIGS. 1 and 2 through a handle part of an obturator of the needle set;

FIG. 4 is an enlarged detailed representation of the region IV of FIGS. 1 and 3;

FIG. 5 is a side view of an obturator of the needle set according to the invention;

FIG. 6 is a side view of a hollow needle of the needle set according to the invention;

FIG. 7 is a plan view of the handle part of the hollow needle of FIG. 6;

FIG. 8 shows a longitudinal section through the obturator of FIG. 5;

FIG. 9 is a plan view of the proximal end of the obturator of FIGS. 5 and 8;

FIG. 11 shows a longitudinal section through the surgical needle set according to the invention according to FIG. 1;

FIG. 12 is a plan view of the proximal end face of the needle set of FIG. 11;

FIG. 13 is an enlarged representation of the distal region YQ of FIG. 11 with the sensor unit inserted into the obturator, with a first embodiment of a proximal sensor;

FIG. 14 is an enlarged representation of the region X of FIG. 11 with the proximal sensor; and FIG. 15 is an enlarged representation of an alternative embodiment of an adapter and the proximal sensor arranged there.

Figure 10:
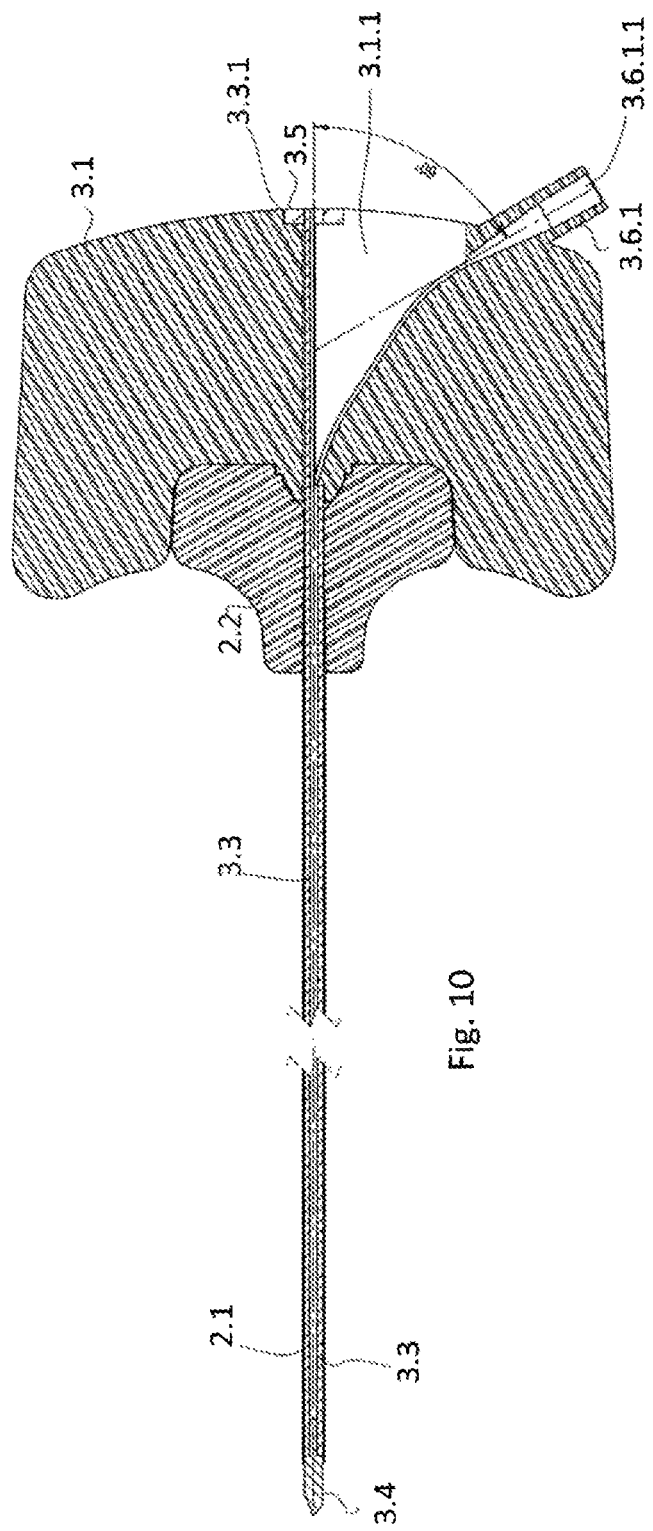
FIG. 10 shows a longitudinal section through the needle set with the obturator inserted through the hollow needle.

The surgical needle set 1 according to the invention essentially comprises a hollow needle 2, an obturator 3 and a sensor unit 4 (FIG. 11).

The hollow needle 2 (FIG. 6) is in the form of a trephine and has a hollow needle tube 2.1, preferably made of stainless steel, and a handle part 2.2, preferably made of plastics material, such as polypropylene, connected to said tube at the proximal end. The two parts 2.1 and 2.2 are inseparably linked, i.e., they cannot be separated without being destroyed. The hollow needle tube 2.1 is provided at its distal end 2.3 with a sharp end-face circular circumferential edge. For this purpose, the outer wall face of the hollow needle tube extends obliquely inward toward the radius of the inner wall face.

The handle part 2.2 is T-shaped and has, at its lateral ends, two rigid tabs 2.4 which come into engagement with lateral recesses 3.2 of a handle part 3.1 of the obturator 3 by pushing the obturator 3 into the hollow needle 2 and relative pivoting of the parts 2 and 3 in order to secure the two parts 2 and 3 to one another.

The obturator 3 (FIG. 5) has a hollow obturator tube 3.3, the already mentioned handle part 3.1, as well as a solid distal tip and a fixing ring 3.5.

The parts 3.3 to 3.5 consist of metal, preferably likewise of stainless steel, and are fixedly interconnected, preferably by welding. The tip 3.4 is in the form of a sharp, pointed trocar. The retaining ring 3.5 is fixedly and non-detachably connected, by the welding process just mentioned, to the proximal end of the obturator tube 3.3 after the obturator tube 3.3 has been inserted by the distal face through the handle part 3.1 of the obturator 3 until it reaches a proximal depression in the handle part 3.1, into which depression the fastening ring 3.5 is inserted for connection to the obturator tube 3.3 (FIGS. 9 and 10). The obturator tube 3.3 can additionally or alternatively be injected as an insert in the handle part 3.1 in the proximal region.

The region of the obturator tube 3.3 of the obturator 3 located in the handle part 3.1 is in the form of merely a half-tube, with a jacket wall 3.3.1 extending over only half the circumference, while said obturator tube is in the form of a fully closed tube across its main region that protrudes relative to the handle part 3.1. The handle part 3.1 has a slot 3.1.1 opposite the opening of the partial tube 3.3.1, which slot extends to a male adapter part 3.6.1, such as a Luer adapter, formed in one piece with the handle part, the passage 3.6.1.1 of which adapter part opens into the slot 3.1.1. A continuous hollow-space connection between the adapter part 3.6.1 and the interior of the obturator tube 3.3 via the slot 3.1.1 is provided in such a manner (in particular FIG. 10).

A female adapter part 3.6.2 of the adapter 3.6, which female adapter part has an internal thread, can be connected to the male adapter part 3.6.1 of the adapter 3.6, which male adapter part has an external screw thread (FIGS. 11 and 14). The adapter part 3.6.2 also has contact lines of a sensor unit 4.

The sensor unit 4 has, distally to the adapter 3.6, two insulated electrical conductors 4.1, 4.2 (FIGS. 13 and 14) in a hose 4a, which conductors are connected at their ends to a distal sensor 4.3 in the form of an electromagnetic coil, namely the conductor 4.1 is connected to the proximal end of the sensor 4.3, while the conductor 4.2 extends through the interior of the coil-shaped sensor 4.3 to its distal end and there is connected to the distal end of the sensor 4.3. These electrically conductive parts of the sensor unit 4 are sheathed by an insulating jacket. Proximally, the sensor unit 4 has a further proximal sensor 4.5, which is designed in the same way as the sensor 4.3 (FIG. 14). When the sensor unit 4 is completely inserted into the obturator through the male adapter part 3.6.1, the distal sensor 4.3 coming to lie inside the obturator tube 3.3 near the tip 3.4 of the obturator, the proximal sensor 4.5 is located in the angled male adapter part 3.6.1 of the adapter 3.6.

In the embodiment shown in FIG. 14, the sensor unit 4 also has a female adapter part 3.6.2 and a proximal sensor 4.5, which is also in the form of a coil and is connected to two conductors 4.6, 4.7.

In the embodiment of FIG. 14, the proximal sensor 4.5 is arranged distally to the adapter part 3.6.2 in the hose 4a of the sensor within and in connection with the adapter parts 3.6.1, 3.6.2 of the adapter part 3.6.

The sensor unit 4 is fixedly connected to a cable 5; its conductors 4.1, 4.2, 4.6, 4.7 lead through the cable 5 to the proximal connection end 5.2 thereof (FIG. 1), by means of which end the cable 5 can be detachably connected to an electronic evaluation device.

The adapter parts 3.6.1, 3.6.2 are oriented at an angle α of 60° with respect to the axis of the obturator tube 3.3 (as shown in FIG. 10). The angle α has to be unequal to 0, but otherwise it can be largely arbitrary; it only has to differ from corresponding orientations of cavities of other surgical instruments, in which cavities the sensors 4.3, 4.5 are secured, so that by detecting the angular orientation between the sensor 4.3 and the sensor 4.5 when inserted in an instrument, the corresponding surgical instrument can be identified and, in the present case, in particular the Jamshidi needle provided herein can be identified. In this respect, the angle can also include a fixed value between 55° and 65° or between, for example, 40° and 80°.

By means of the invention, the surgical instrument used, here a Jamshidi needle, can be detected in advance by an electric field being generated by the generator of an electromagnetic field, and an evaluation unit not only the different positions of the two sensor coils 4.3, 4.5 and their longitudinal distance from one another, but also their angular orientation given by the corresponding surgical instrument (herein a Jamshidi needle) via the field signals detected by the sensors 4.3, 4.5 being determined.

Furthermore, the invention provides in the usual way the determination of the location of the distal end of the surgical instrument 1 in the patient during the operation and, due to the different orientation of the sensors 4.3, 4.5, also the orientation of the instrument itself in space.

For this purpose, the sensor unit 4 is introduced in advance, i.e., before performing a surgical step, into the surgical instrument 1, here more precisely the obturator 3 of the surgical instrument, via the adapter part 3.6.1, both the sensor unit 3 and the cable 5 leading to the evaluation unit (not shown) being secured to the male adapter part 3.6.1 by means of the female adapter part 3.6.2 of the adapter 3.6, as a result of which the position of the sensor unit 3 and thus that of the sensors 4.3, 4.5 in the surgical instrument 1 and in particular in the obturator 3 is precisely defined, as is their relative alignment owing to the positioning of the sensors 4.3, 4.5, which have a fixed specified distance from one another on the sensor unit.

The invention claimed is:

1. A surgical needle set, the set comprising:
   a hollow needle; and
   an obturator, wherein the obturator comprises a hollow space extending longitudinally in a proximal direction starting at a finite distance from a distal tip thereof, wherein at least one proximal lateral outlet of the hollow space is provided within a handle part of the obturator, and the hollow space is in connection with a passage of a male adapter part of an adapter, which passage extends at a finite angle to the longitudinal extent of the hollow space, wherein an obturator tube of the obturator in a region located in a handle part is in a form of a half-tube with a jacket wall extending over only half a circumference and the handle part has a slot which extends to the male adapter part formed in one piece with the handle part, the passage of the male adapter part opening into the slot.

2. The set according to claim 1, further comprising a sensor unit comprising a distal sensor and a proximal sensor that extends through the passage of the adapter part to the distal end of the hollow space, the orientation of said proximal sensor enclosing a finite angle to the orientation of the distal sensor due to the adapter part.

3. The set according to claim 2, wherein a relative angle between the distal sensor and the proximal sensor is between 10° and 90°.

4. The set according to claim 2, wherein the sensor unit is formed in the female adapter part.

5. The set according to claim 2, wherein the sensor unit is inseparably connected to a connection cable.

6. The set according to claim 5, wherein the connection cable has a connection end for connection to an evaluation unit.

7. The set according to claim 2, wherein the sensors of the sensor unit are in the form of coils, to distal and proximal ends of each of which an electrical line is respectively connected.

8. The set according to claim 1, wherein a distal end of the obturator is in the form of a trocar.

9. The set according to claim 1, wherein the obturator tube is secured to the handle part of the obturator by means of a fixing ring fixedly connected to said tube.

10. The set according to claim 1, wherein the male adapter part of the obturator is in the form of a Luer adapter part.

11. The set according to claim 1, wherein the hollow needle and the obturator are detachably connectable by means of rigid tabs of the handle part of the hollow needle, which tabs engage in lateral recesses of the handle part of the obturator.

12. The set according to claim 1, wherein the hollow needle is in the form of a trephine.

13. An obturator, comprising:
   a handle part, the obturator defining a hollow space extending longitudinally in a proximal direction starting at a finite distance from a distal tip thereof, wherein at least one proximal lateral outlet of the hollow space is provided within the handle part, and the hollow space is in connection with a passage of a male adapter part of an adapter, which passage extends at a finite angle to the longitudinal extent of the hollow space;
   an obturator tube in a region located in the handle part being in a form of a half-tube with a jacket wall extending over only half a circumference, the handle part having a slot extending to the male adapter part formed in one piece with the handle part, the passage of the male adapter part opening into the slot.

14. A method for determining the position of a surgical instrument the method comprising the steps of:
   providing the surgical instrument, wherein the surgical instrument comprises a hollow needle; and an obturator located in said needle, wherein an obturator tube of the obturator in a region located in a handle part is in a form of a half-tube with a jacket wall extending over only half a circumference;

connecting the hollow needle and the obturator relative to one another so as to have fixed positions, but so as to be detachable;

configuring the obturator such that the obturator has, starting a finite distance from a distal tip thereof, a hollow space extending longitudinally in a proximal direction;

providing at least one proximal lateral outlet of the hollow space within a handle part of the obturator;

providing the hollow space in connection with a passage of a male adapter part of an adapter, which passage extends at a finite angle to the longitudinal extent of the hollow space, the handle part having a slot extending to the male adapter part formed in one piece with the handle part, the passage of the male adapter part opening into the slot; and arranging an angular orientation of two sensors of a sensor unit, which sensors are arranged at a fixed longitudinal distance from one another.

* * * * *